United States Patent [19]

Sato et al.

[11] 3,957,579

[45] May 18, 1976

[54] METHOD FOR PREPARING D-TARTARIC ACID

[75] Inventors: Eiji Sato, Zushi; Akira Yanai, Kamakura, both of Japan

[73] Assignee: Toray Industries, Inc., Tokyo, Japan

[22] Filed: Apr. 24, 1975

[21] Appl. No.: 571,222

[30] Foreign Application Priority Data

Apr. 30, 1974  Japan.............................. 49-47525

[52] U.S. Cl. ................................................. 195/30
[51] Int. Cl.² .......................................... C12B 1/00
[58] Field of Search..................... 195/30, 47, 66 R; 424/317

[56] References Cited

UNITED STATES PATENTS 2,972,566    2/1961    Kitahara .............................. 195/30

*Primary Examiner*—A. Louis Monacell
*Assistant Examiner*—C. A. Fan

[57] ABSTRACT

Dextro or d-tartaric acid is prepared by microbial conversion of cis-epoxysuccinic acid which is subjected to asymmetrical hydrolysis by the catalytic action of a microorganism taken from the group consisting of the genera Achromobacter and Alcaligenes in which cis-epoxysuccinic acid in an aqueous solution is brought into contact with the enzyme d-tartrate epoxidase.

12 Claims, No Drawings

METHOD FOR PREPARING D-TARTARIC ACID

BRIEF SUMMARY OF THE INVENTION

Heretofore, d-tartaric acid has been produced solely from crude tartar which is a by-product obtained in the production of wine. It is known that tartaric acids other than those in natural form such as dl- or meso-tartaric acid, may be prepared by chemical or biochemical methods. However, artificial forms of tartaric acid are clearly different from the natural form in various properties, particularly when used as a food additive.

The present invention is a method for producing d-tartaric acid by microbiological conversion of cis-epoxysuccinic acid to d-tartaric acid. According to this invention, the hydrolyzing activity of the microorganisms belonging to the genera Achromobacter and Alcaligenes, and the enzymes produced by said microorganisms, brings about the conversion of cis-epoxysuccinic acid to d-tartaric acid via a selective hydrolytic step, whereby the desired product is readily obtained in substantially pure form and in quantity.

Therefore, it is an object of the present invention to produce d-tartaric acid which is substantially pure in form by microbiological conversion.

It is a further object of the present invention to produce d-tartaric acid easily and in quantity, utilizing the microbiological conversion method of the present invention.

These and other objects of the present invention will become more readily apparent from the following detailed description and examples.

DETAILED DESCRIPTION OF THE INVENTION

Cis-epoxysuccinic acid for use in this invention can be easily and inexpensively prepared from maleic anhydride. The reaction of this invention is represented as the following equation in which the above mentioned previous steps starting with maleic anhydride are included.

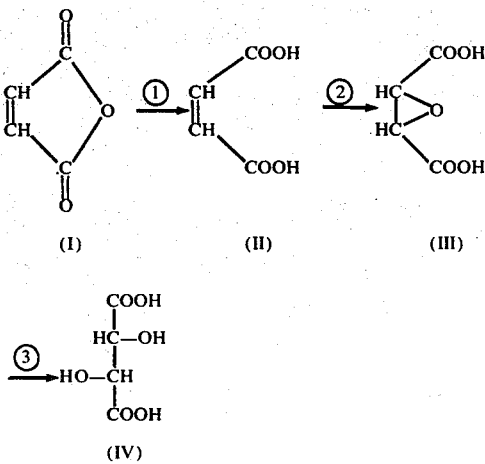

In the above equation, ① is a reaction easily conducted by dissolving maleic anhydride in water, ② is a reaction producing cis-epoxysuccinic acid from maleic acid, for example by reacting maleic acid with hydrogen peroxide in the presence of an epoxidizing catalyst such as sodium tungstate, and ③ is a reaction achieved according to this invention.

The cis-epoxysuccinic acid-hydrolyzing activity of this invention is obtained by cultivating microorganisms belonging to the genera Achromobacter or Alcaligenes. Examples of such microorganisms employed in this invention include the following bacterial strains: Achromobacter tartarogenes nov. sp. TORAY 1246, FERM-P 2507, Achromobacter epoxylyticus nov. sp. TORAY 1270, FERM-P 2508, Achromobacter acinus nov. sp. TORAY 1366, FERM-P 2509, Achromobacter sericatus nov. sp. TORAY 1190, FERM-P 2510, Alcaligenes epoxylyticus nov. sp. TORAY 1128, FERM-P 2511, Alcaligenes margaritae nov. sp. TORAY 1110, FERM-P 2512 ("FERM-P" is the official deposit number of each organism in the Fermentation Research Institute in Japan).

Regarding the composition of the culture medium when cultivating such microorganisms, either a synthetic or a natural culture medium is suitable so long as it contains the essential nutrients for the growth of the microorganisms employed, and a small amount of cis-epoxysuccinic acid, its salt, and d-tartaric acid or its salt is used as the inducer for the enzyme. Such an inducer can be added either before or during the cultivation.

As the source of carbon in the culture medium, well known ingredients, for example, sugars such as glucose or saccharose, alcohols, organic acid, corn steep liquor or molasses as well as cis-epoxysuccinic acid, d-tartaric acid or its salts can be added. As the source of nitrogen, ingredients, also well known, can be added, for example, ammonia, ammonium salts such as ammonium sulfate or ammonium chloride, amide compounds, nitrate, urea, amino acids or proteins such as peptone, soy bean powder or meat extract. Other ingredients such as phosphates, sulfates, salts of magnesium, potassium, zinc, iron, manganese or other metals, yeast extract, vitamin or nucleotide can be added as in the well known cultivation of microorganisms. The cultivation is preferably carried out aerobically at 20° C – 35° C, more preferably 26° C – 30° C. The pH of the culture medium is preferably in the range of 6 – 8. The enzyme, "d-tartrate epoxidase", accumulates in the cells as the cultivation proceeds.

As for the state of the cis-epoxysuccinic acid-hydrolyzing agent when applied in the method of this invention, a growing culture, a culture broth, living cells, a cell extract, treated cells such as acetone dried cells, toluene dried cells, lyophilized cells, and an enzyme, namely, "d-tartrate epoxidase" are effectively used. Of course, the enzyme can be used also in the state of an "insolublized enzyme" such as DEAE-, TEAE-, GE-cellulose-absorbed enzyme and DEAE-"Sephadex"-absorbed enzyme.

In connection with the reaction step of this invention, preferred embodiments are as follows. The reaction mixture is composed of a proper amount of cis-epoxysuccinic acid-hydrolyzing agent and an aqueous solution of cis-epoxysuccinic acid. Cis-epoxysuccinic acid is added to the reaction mixture as the free acid or as its salt. Essentially any kind of salt can be used, but from the economical point of view, alkali metal or alkaline earth metal salts such as sodium, potassium, calcium or ammonium salts are preferred. Essentially, there is no restriction on the range of concentration of the cis-epoxysuccinic acid. Usually, 10 – 25% (w/v) of cis-epoxysuccinic acid (or its salt) is preferably added in the reaction mixture at the beginning of the reaction.

The pH of the reaction mixture is preferably maintained between 6.5 – 9.0, more preferably 7.0 – 8.0. For the adjustment of the pH of the reaction mixture, alkaline metal hydroxide and the like can be employed. The reaction is conducted at any temperature conducive to satisfactory stability of the enzyme, for example, about 20° – 50° C. The temperature may be 50° C in the case of 2 – 3 hours of reaction, or 40° C in the case of the reaction longer than 20 hrs. at which cis-epoxysuccinic acid is substantially stoichiometrically converted to d-tartaric acid.

A variety of well known procedures can be employed in the recovery of d-tartaric acid from the reaction mixture.

For example, the reaction mixture, or the filtrate resulting from its filtration is passed through a column filled with an anion exchange resin to absorb d-tartaric acid. After washing the column, absorbed d-tartaric acid is eluted by a suitable acid such as formic acid. d-Tartaric acid can be obtained from the resulting eluate by a simple evaporation and crystallization procedure.

Recovery of d-tartaric acid is also effected by the addition of a calcium salt to the reaction mixture. Calcium sulfate, calcium chloride and calcium carbonate are preferred. After adding one of these calcium salts to the reaction mixture, d-tartaric acid is recovered from the reaction mixture as calcium d-tartrate by simple filtration (usually with $4H_2O$). The salt is preferably converted to the free acid by conventional methods.

The six microorganisms mentioned above have characteristics as shown in Tables 1 and 2. For these taxonomic investigations, "Bergey's Manual of Determinative Bacteriology", 7th edition (1957) (referred to as "the Manual" hereafter) applies. The four strains of microorganisms listed in Table 1 are classified as novel species in the genus Achromobacter. All of them are Gram negative cocci or short rods, aerobic, non-motile and achromogenic. No gas formation was observed from the sugars. Microorganisms having the foregoing characteristics also belong to the genus Neisseria.

According to the Manual, however, all microorganisms which belong to the genus Neisseria are animal parasites and have an optimal growth temperature of 37° C whereas the microorganisms of this invention are originally isolated from soil and cannot grow at 37° C. Hence we do not consider it appropriate to classify these microorganisms as Neisseria.

There have been many opinions on microorganisms which are Gram negative, achromogenic and non-motile. For example, Prevot proposed to establish a new genus Acinetobacter to include these microorganisms. ("Traite de Systematique Bacterienne", Vol. 2, pgs. 156–164 (1961)). The microorganisms which are the subject of this invention have the characteristics of Acinetobacter of Prevot. However, to avoid confusion, we have adopted the classification system of the Manual in which Prevot's Acinetobacter are classified as Achromobacter. Among the species of Achromobacter in the Manual, three are shown to be non-motile and devoid of gelatin liquefaction. Among these three, Achromobacter eurydice has no action on litmus milk or on sugars other than glucose. Achromobacter delmarvae does not produce $H_2S$ and causes browning of milk. Achromobacter parvulus makes punctiform colonies and has a strong tendency to form ammonia. The microorganisms in question are not identical to the known Achromobacter in the above mentioned characteristics. Therefore, we have concluded that the microorganisms of this invention are novel species of Achromobacter.

Two strains of microorganisms listed in Table 2 are distinguished from Achromobacter by the fact that they show alkaline reaction in litmus milk and do not produce any acid from sugars.

Based upon these considerations, we have classified these microorganisms as Alcaligenes. Two known species of Alcaligenes, Alcaligenes viscolactis and Alcaligenes metalcaligenes, have some similarities to the microorganisms of this invention. However the former is characterized by its tendency to make milk highly viscous and the latter is an inhabitant of the intestinal tract and has an optimal growth temperature of 22° C. Therefore, we have concluded that the microorganisms of this invention are novel species of Alcarigenes.

In addition to the above described microorganisms, the use of other Achromobacter or Alcaligenes species producing the enzyme d-tartrate epoxidase is preferred. It is also to be understood that for the production of d-tartaric acid, this invention is not limited to the use of the so-called wild type of microorganisms. It is desired and is intended to include the use of mutants produced by well known means from the microorganisms described, such as by ultraviolet irradiation, phage exposure, nitrosoguanidine treatment, and the like.

The following Tables 1 and 2 illustrate in detail the characteristics and function of microorganisms which are used in accordance with the method of this invention.

Table 1

| Name of species | Achromobacter tartarogenes nov. sp. | Achromobacter epoxylyticus nov. sp. | Achromobacter acinus nov. sp. | Achromobacter sericatus nov. sp |
|---|---|---|---|---|
| No. | TORAY 1246 | TORAY 1270 | TORAY 1366 | TORAY 1190 |
| FERM-P | FERM-P 2507 | FERM-P 2508 | FERM-P 2509 | FERM-P 2510 |
| Morphological properties | 0.8 – 1.2μ × 0.8 – 1.8μ coccoid to short rods. Cells accompanied by slimy material Occur singly, non-motile, asporogenic, Gram negative. | Same | Same | Same |
| Nutrient agar colonies | Circular, entire, umbonate to convex, smooth, viscid, whitish brown, opaque. | Circular, entire, convex, smooth, liquid, brownish white, translucent. | Circular, entire, umbonate to convex, smooth, viscid, whitish brown, opaque. | Circular, entire, smooth, convex, whitish brown, opaque |
| Nutrient agar slant | Filliform, growth moderate, whitish brown, no chromogenesis | Same | Same | Same |
| Nutrient broth | Moderately turbid, viscid sediment, no pellicle. | Moderately turbid, viscid sediment, thin | Moderately turbid, viscid sediment, no pellicle | Moderately turbid, viscid |

Table 1-continued

| | Achromobacter tartarogenes nov. sp. | Achromobacter epoxylyticus nov. sp. | Achromobacter acinus nov. sp. | Achromobacter sericatus nov. sp |
|---|---|---|---|---|
| Name of species | | | | |
| No. | TORAY 1246 | TORAY 1270 | TORAY 1366 | TORAY 1190 |
| FERM-P | FERM-P 2507 | FERM-P 2508 | FERM-P 2509 | FERM-P 2510 |
| | | pellicle. | | sediment, thin pellicle. |
| Cis-epoxysuccinate agar slant | Filliform, white, translucent, moderate growth, opalescent. No chromogenesis. | Same | Same | Same |
| Potato agar slant | Filliform, slightly brownish white, opaque, growth abundant, no chromogenesis. | Same (color more whitish than others) | Same | Same |
| Gelation Stab | No liquefaction | | Same | Same | Same |
| BCP milk | Turns pale blue within 2-3 days. Returns neutral within a week. After 15 days, milk coagulates and becomes yellow. No peptonization. | | Same | Same | Same |
| Physiological Properties | | | | |
| 1. Reduction of nitrate | − | | − | + | + |
| 2. Denitrification | − | | − | − | − |
| 3. Methyl red test | − | | − | − | − |
| 4. Voges Proskauer test | − | | − | − | − |
| 5. Indole | − | | − | − | − |
| 6. H$_2$S (Cystein medium) | Strongly produced | | Produced | Produced | Produced |
| 7. Hydrolysis of starch | − | | − | − | − |
| 8. Utilizaton of citrate | | | | | |
| Koser's medium | + | | + | + | + |
| Christensen's medium | + | | + | + | + |
| 9. Urease | + | | + | + | + |
| 10. Oxidase | + | | + | + | + |
| 11. Catalose | + | | ∓ | + | + |
| 12. Gas from sugar | None | | None | None | None |
| 13. Acid from sugar | Small amounts from arabinose and xylose. Slight from fructose, mannose, very slight from glucose, no acid from galactose, lactose, saccharose, starch and sorbitol. | | Same (A little more acid produced than others) | Same | Same |
| pH relations | 6 − 9 | | 5 − 10 | 5 − 10 | 6 − 9 |
| Temperature relations | Optimal temperature 26 − 30° C. Scanty growth at 37° C. | | Same | Same | Same |

Table 2

| | Alcaligenes epoxylyticus nov. sp. | Alcaligenes margaritae nov. sp. |
|---|---|---|
| Name of species | | |
| No. | TORAY 1128 | TORAY 1110 |
| FERM-P | FERM-P 2511 | FERM-P 2512 |
| Morphlogical properties | 0.8 − 1.2μ × 0.8 − 2.0μ. Coccoid to short rods. Cells, accompanied by slimy material, occur singly, Non-motile, asporogenic, Gram negative. | Same |
| Nutrient agar colonies | Circular, entire, umbonate to convex, smooth, butyrous, opaque. | Circlar, entire, convex, smooth, viscid to butyrous, opaque, puncti form. |
| Nutrient agar slant | Filliform, growth moderate, brownish white, no chromogenesis. | Same |
| Nutrient broth | Moderately turbid, granular sediment, very thin, oily pellicle. | Same |
| Cis-epoxysuccinate agar slant | Filliform, white, translucent, growth moderate, opalescent, no chromogenesis. | Same |
| Potato agar slant | Filliform, white, opaque growth abundant, smooth, glistening, viscid, no chromogenesis. | Same |
| Gelatin stab | No liquefaction. | Same |
| BCP milk | Becomes blue within 2 − 3 days. No further change. No coagulation or peptonization. | Same |
| Physiological properties | | |
| 1. Reduction of nitrate | + | − |
| 2. Denitrification | − | − |
| 3. Methyl red test | − | − |
| 4. Voges Proskauer test | − | − |
| 5. Indole | − | − |
| 6. H$_2$S (cystein medium) | Strongly produced | Strongly produced |
| 7. Hydrolysis of starch | − | − |

Table 2-continued

| Name of species | Alcaligenes epoxylyticus nov. sp. | Alcaligenes margaritae nov. sp. |
|---|---|---|
| No. | TORAY 1128 | TORAY 1110 |
| FERM-P | FERM-P 2511 | FERM-P 2512 |
| 8. Utilization of citrate | | |
|    Koser's medium | — | — |
|    Christensen's medium | — | — |
| 9. Urease | Weakly positive | Weakly positive |
| 10. Oxidase | + | + |
| 11. Catalase | + | + |
| 12. Gas from sugar | None | None |
| 13. Acid from sugar | No acid from glucose, fructose, mannose, xylose or arabinose. | Same |
| pH relations | 6 – 9 | 6 – 10 |
| Temperature-growth relations | Optimal temperature 26 – 30° C. No growth at 37° C. | Same |

The present invention will be explained in further detail in the following examples. In these examples, an enzyme activity which forms 1μ (micro) mole of d-tartaric acid in 1 hour is expressed as 1 unit. d-Tartaric acid is assayed using ammonium metavanadate by the method of Maurer (Weinberg. Keller, Vol. 14, pp. 323 – 328 (1967)). Cis-epoxysuccinic acid is synthesized by the method of Payne & Williams. (Journal of Organic Chemistry, Vol. 24, pp. 54 – 55 (1959)). Hereinafter "Achromobacter" will be referred to as "Ach." and "Alcaligenes" as "Alc."

EXAMPLE 1

Ach. tartarogenes nov. sp. TORAY 1246 (FERM-P 2507) was inoculated into a medium consisting of 0.5% disodium cis-epoxysuccinate, 0.2% ammonium sulfate, 0.14% potassium dihydrogen phosphate, 0.31% disodium hydrogen phosphate (12 hydrate), 0.05% magnesium sulfate (7 hydrate) and 0.05% yeast extract (Difco). The pH of the medium was adjusted to 7.2 before sterilization at 120° C for 15 minutes. Cells were grown aerobically at 30° C for 36 hours and were harvested by centrifugation when a stationary phase was reached. After being washed with distilled water, cells were frozen at −20° C and thawed at room temperature. About 108 mg (dry weight) of cells with 1270 units of d-tartrate epoxidase activity were obtained from 120 ml of the culture broth.

To the aqueous suspension of the cells, 3.0 g of disodium cis-epoxysuccinate and 75 mM tris (hydroxymethyl) amino methane-HCl buffer (pH 8.0) were added to make the total volume 20 ml. This mixture was allowed to stand at 37° C for 21.0 hours. After the reaction was completed, 18.2 ml of 1M calcium chloride were added to the mixture. The resulting precipitates of calcium tartrate were collected on a glass filter after being kept overnight at 5° C. The precipitates were suspended in a small volume of distilled water and the suspension was mixed with about 40 ml of Amberlite IR 120 B (H⁺ type) and stirred until it became clear at room temperature. The resin was filtered off and washed with water. Combined filtrates were evaporated to dryness below 60° C under decreased pressure. About 50 ml of 99.5% ethanol was added to the resulting solid material and the insoluble material was removed by filtration. The filtrate was again dried to produce 2.33 g of d-tartaric acid crystal with a yield of 91%. The following characteristics were observed: rotation value $$[\alpha]_D^{20} \ (c = 20, H_2O)$$

authentic d-tartaric acid: +12.4
reaction product: +12.4

EXAMPLE 2

Alc. epoxylyticus nov. sp. TORAY 1128 (FERM-P 2511) was inoculated into the same medium as in Example 1 with the exception that it was enriched with 0.5% glucose. Cells were grown aerobically at 30° C for 38.5 hours and collected, washed and resuspended in a one-fifth volume of distilled water. The d-tartrate epoxidase activity of the suspension was 209 units per ml. Six ml. of the suspension were mixed with 4 g of disodium cis-epoxysuccinate and 50 mM tris (hydroxy methyl) amino methane-HCl buffer (pH 8.0) to make a final volume of 30 ml. This mixture was incubated at 40° C for 24 hours without shaking. To the reaction mixture, 6 ml of 4.5 M calcium chloride were added to recover d-tartaric acid as calcium salt. The resulting precipitates were purified as described in Example 1 to give 3.0 g of d-tartaric acid with a yield of 88%.

EXAMPLE 3

Each of the four strains of organisms listed in the following Table 3 was inoculated into the same medium as in Example 2 and grown aerobically for 36 hours at 30° C. Cells were collected, washed and freeze-thawed as in Example 1. Reaction was carried out using these suspensions and to each was added 0.4 g of disodium cis-epoxysuccinate in 50 mM tris-HCl buffer (pH 8.0) at 40° C. The total volume of the mixture was 3.0 ml. d-Tartaric acid was recovered and purified as described in Example 1. The results are summarized in the following table.

Table 3

| | Enzyme activity (unit/ml) | Reaction time (hr.) | Yield gr. (%) |
|---|---|---|---|
| Ach. epoxylyticus nov. sp. TORAY 1270 FERM-P 2508 | 43.6 | 7.5 | 0.30 (88) |
| Ach. acinus nov. sp. TORAY 1366 | 32.2 | 8.5 | 0.30 (89) |

Table 3-continued

| | Enzyme activity (unit/ml) | Reaction time (hr.) | Yield gr. (%) |
|---|---|---|---|
| FERM-P 2509 | | | |
| Ach. sericatus nov. sp. | | | |
| TORAY 1190 | 28.1 | 10.0 | 0.29 (86) |
| FERM-P 2510 | | | |
| Alc. margaritae nov. sp. | | | |
| TORAY 1110 | 29.8 | 9.0 | 0.28 (81) |
| FERM-P 2512 | | | |

Example 4

The cells of Ach. tartarogenes nov. sp. TORAY 1246 (FERM-P 2507), obtained from 3 liters of the culture broth prepared as described in Example 1, were suspended in 10 mM tris-HCl buffer (pH 7.6) to make 200 ml. The suspension contained 5.3 g of the cells and 34200 units of d-tartrate epoxidase activity. One hundred ml of the suspension were treated by a French Press and a sonic oscillator. To the supernatant fluid resulting from centrifugation at 7000 r.p.m. for 15 minutes of the treated cell suspension, 16.2 g (30% saturation) of ammonium sulfate were added. After being kept at 5° C overnight, the precipitates then formed were removed and discarded by centrifugation. To the resulting clear supernatant fluid, 25.9 g (0.70% saturation) of ammonium sulfate were added. After 7 hours, the precipitates formed were collected by centrifugation and dissolved in tris-HCl buffer (10 mM, pH 7.6) to make 46 ml. The solution was dialyzed to remove dialyzable salts to the buffer overnight at 4° C using a Visking cellophane tube. Eighty-one ml of the partially purified enzyme solution thus obtained contained 1.07 g of protein and 13500 units of d-tartrate epoxidase activity. Fifty ml of 20 (w/v)% disodium cis-epoxysuccinate solution buffered by 50 mM tris-HCl buffer to pH 8.0 were mixed with 17 ml of the enzyme solution and water to make a total volume of 100 ml. The mixture was incubated at 40° C for 24 hours without shaking. After the reaction was completed, 14 ml of 4.5 M calcium chloride was added. Precipitates were collected after overnight maturation and 7.77 g of d-tartaric acid was obtained by the same method as in Example 1, yielding 91 – 92%.

Example 5

Ach. tartarogenes nov. sp. TORAY 1246 (FERM-P 2507) was inoculated into a medium consisting of 1.0% glycerin, 0.2% $NH_4Cl$, 0.31% $Na_2HOP_4$, $12H_2O$, 0.14% $KH_2PO_4$, 0.05% $MgSO_4$, $7H_2O$, 0.02% yeast extract and 0.2% corn steep liquor. The pH of the medium was adjusted to 6.7 at the beginning of the culture and maintained above 6.7 during the culture period using 7% $NH_4OH$.

Cells were grown at 30° C with aeration (20 liters/min) and agitation (300 rpm) in a 30 liters jar fermentor equipped with an automatic pH controller. When the stationary phase was reached, disodium cis-epoxysuccinate was added to give a final concentration of 0.7 (w/v)%. Six hours after the addition of cis-epoxysuccinate, the d-tartrate epoxidase activity reached its maximal value of about 160 units per ml. 4.9 liters of the culture broth were mixed with 15.1 liters of a 1.32 M solution of disodium cis-epoxysuccinate. The mixture was heated to 40° C and the pH of the mixture was adjusted to 7.5 using dilute HCl. The reaction was conducted at 40° C and the pH was maintained between 7.5 and 7.7 for 27 hours. After completion of the reaction, the pH of the mixture was adjusted to 6.0 using 6N. HCl and 2.79 kg of $CaSO_4.2H_2O$ were added to 13.8 liters of the mixture. The mixture was agitated for 1 hour. The Ca tartrate then formed was collected by filtration and washed with distilled water. The resulting washed cake of Ca tartrate (about 4.6 kg) was suspended in water. d-Tartrate was liberated by the addition of an amount of $H_2SO_4$ equivalent to Ca tartrate, to the slurry. The crude d-tartaric acid solution (obtained by filtration which served to remove $CaSO_4$ from the mixture) was passed through a column packed with SK1B ($H^+$ type) cation exchange resin to remove Ca ion and other cations. The decationized solution was further purified by the addition of $BaCO_3$ to remove $SO_4$ ion, and by the addition of active charcoal to remove other impurities.

After removing the $BaSO_4$ and active charcoal by filtration, a clear solution of purified d-tartaric acid was obtained. This solution contained 94% of d-tartaric acid as compared with that present in the Ca tartrate cake in the first stage of the purification procedure. The concentration of the solution produced 1.65 kg of d-tartaric acid.

The following is claimed:

1. A method for preparing d-tartaric acid which comprises asymmetrically hydrolysing cis-epoxysuccinic acid in an aqueous medium in the presence of a microorganism selected from the group consisting of the genera Achromobacter and Alcaligenes having cis-epoxysuccinic acid-hydrolysing activity.

2. The method according to claim 1 wherein said cis-epoxysuccinic acid in an aqueous medium is contacted with and subjected to the action of a member of the group consisting of growing culture, a culture broth, living cells, dried cells, and a cell extract of a microorganism having cis-epoxysuccinic acid-hydrolysing activity selected from the genera Achromobacter and Alcaligenes, said cis-epoxysuccinic acid undergoing asymmetrical hydrolysis in contact with said group member.

3. A method for preparing d-tartaric acid which comprises contacting cis-epoxysuccinic acid in an aqueous medium with the enzyme d-tartrate epoxidase, said cis-epoxysuccinic acid undergoing asymmetrical hydrolysis in contact with said enzyme.

4. The method according to claim 3 in which said enzyme is isolated from cells of a microorganism having cis-epoxysuccinic acid-hydrolysing activity selected from the genera Achromobacter and Alcaligenes.

5. The method according to claim 3 in which the enzyme which is used for the asymmetrical hydrolysis of cis-epoxysuccinic acid is cultivated in an aqueous nutrient medium containing cis-epoxysuccinic acid or d-tartaric acid as the enzyme inducer under submerged aerobic conditions until substantial growth is achieved.

6. The method according to claim 1 in which the conversion of cis-epoxysuccinic acid to d-tartaric acid is conducted at a pH of about 6.5 to about 9.

7. The method according to claim 3 in which the conversion of cis-epoxysuccinic acid to d-tartaric acid is conducted at a pH of about 6.5 to about 9.

8. The method according to claim 1 in which the d-tartaric acid so produced in the reaction mixture is then isolated.

9. The method according to claim 2 in which the d-tartaric acid so produced in the reaction mixture is then isolated.

10. The method according to claim 6, wherein said pH is about 7.0 – 8.0.

11. The method according to claim 1, wherein the reaction temperature is about 20° – 50° C.

12. The method according to claim 11, wherein the reaction temperature is about 40° C and the cis-epoxysuccinic acid is substantially stoichiometrically converted to d-tartaric acid.

* * * * *